United States Patent [19]

Cehovic

[11] 3,988,442
[45] Oct. 26, 1976

[54] CYCLIC NUCLEOTIDE DERIVATIVES FOR TREATMENT OF HYPOTHYROIDISM

[75] Inventor: Georges D. Cehovic, Santa Ana, Calif.

[73] Assignee: Nelson Research & Development Company, Irvine, Calif.

[22] Filed: July 16, 1975

[21] Appl. No.: 596,380

[52] U.S. Cl. .................................. 424/180; 536/27
[51] Int. Cl.² ........................................ A61K 31/70
[58] Field of Search ............... 424/180; 260/211.5 R

[56] References Cited
UNITED STATES PATENTS
3,856,776  12/1974  Cehovic et al. .................... 424/180

*Primary Examiner*—Lewis Gotts
*Assistant Examiner*—Cary Owens
*Attorney, Agent, or Firm*—Martin A. Voet

[57] ABSTRACT

A method for stimulating the production of thyroid stimulating hormone (TSH) and enhancing thyroid function in animals comprising administering to an animal having low thyroid function an effective amount of a cyclic nucleotide derivative having the structural formula

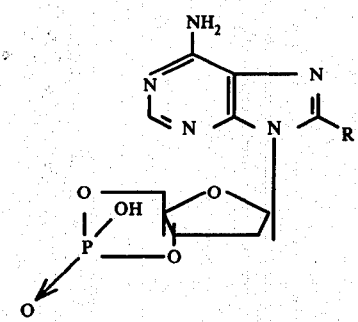

wherein R is selected from the group consisting of amino, thiomethyl and azido and pharmaceutically acceptable salts thereof.

1 Claim, 3 Drawing Figures

CYCLIC NUCLEOTIDE DERIVATIVES FOR TREATMENT OF HYPOTHYROIDISM

BACKGROUND OF THE INVENTION

1. Field of the Invention

The present invention generally relates to a method for stimulating the production of thyroid stimulating hormone (TSH) and enhancing thyroid function in animals. More particularly, the present invention relates to a method for treatment of hypothyroidism.

2. Background of the Prior Art

Cyclic 3',5'-adenosine monophosphate (cyclic AMP) is now recognized as a versatile regulatory agent which acts to control the rate of a number of cellular processes. It occurs in virtually all animal species.

It is now believed that thyrotropin releasing hormone (TRH) produced in the hypothalmus stimulates adenyl cyclase (an enzyme which produces cyclic AMP in the body from adenosine triphosphate) in the thyrotropic cells of the anterior pituitary gland. The resulting rise in the level of cyclic AMP in these cells stimulates the release of thyroid-stimulating hormone (TSH), which then stimulates adenyl cyclase in the thyroid gland. This results in an increase in the level of cyclic AMP which in turn increases the synthesis and the release of thyroid hormone.

In vitro stimulation of thyroid stimulating hormone (TSH) release from the pituitary gland by exogenous cyclic AMP or its dibutyryl derivative, $N^6,2'O$-dibutyryl cyclic AMP (DBC) has been heretofore shown. It has also been shown that in vitro administration of exogenous cyclic AMP or DBC stimulates synthesis and release of thyroidal hormone from the thyroid gland. However, in vivo studies even with very high doses of cyclic AMP have shown only a small effect on thyroidal function.

Hypothyroidism is a condition resulting from deficiency of thyroid activity. Hypothyroidism is treatable with human thyroid stimulating hormone (TSH), but long-term treatment can result in undesirable side effects. Hypothyroidism is also treatable with extracts of animal thyroid glands. However, not all hypothyroid persons respond to this treatment and there are also undesirable side effects.

SUMMARY OF THE INVENTION

I have now discovered that certain cyclic AMP derivatives stimulate production of TSH and enhance thyroidal function when administered to animals, an effect at least one order of magnitude greater than that of cyclic AMP. In addition, it has been discovered that these cyclic nucleotide derivatives also increase the secretion of thyroxin. This discovery opens the possibility of using particular derivatives of cyclic AMP with relative specificity on thyroidal function.

The present invention relates to a method for stimulating the production of TSH and enhancing thyroidal function comprising administering to an animal an effective amount of a cyclic nucleotide derivative having the structural formula

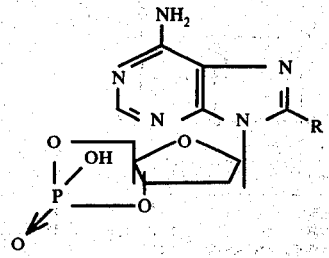

wherein R is selected from the group consisting of amino, thiomethyl and azido and pharmaceutically acceptable salts thereof.

The present invention further relates to a method of temporarily alleviating the signs and symptoms of hypothyroidism in humans comprising administering to a hypothyroid human an effective amount of the above-identified cyclic nucleotide derivative.

DETAILED DESCRIPTION OF THE INVENTION

Figure 1:
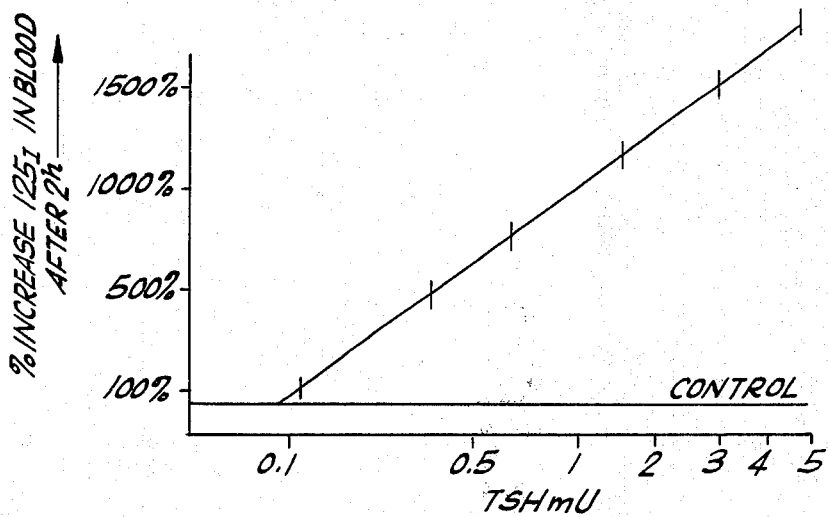
FIG. 1 shows a log dose response for thyroid stimulating hormone (TSH).

The cyclic AMP derivatives of the present invention may be made according to methods known in the prior art, e.g. U.S. Pat. No. 3,712,885.

Pharmaceutically acceptable salts which may be used in the present invention are the conventional non-toxic pharmaceutical salts and are generally obtained by neutralizing the free acid with a suitable base, e.g. neutralization with NaOH forms the sodium salt.

The term "animals" is used herein to refer to higher animals including domesticated animals and warm blood pets as well as human beings.

The term "method of treatment of hypothyroidism" is used herein to refer to the method whereby the signs and symptoms of hypothyroidism are temporarily reduced or alleviated.

The compounds of the present invention may be utilized in pharmaceutical compositions. Generally, pharmaceutical compositions may be in a form suitable for oral use, for example, as tablets, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are suitable for manufacture of tablets. These excipients may be, for example, inert diluents, for example calcium carbonate, sodium carbonate, lactose, calcium phosphate or sodium phosphate; granulating and disintegrating agents, for example maize starch, or alginic acid; binding agents, for example starch, gelatine or acacia, and lubricating agents, for example magnesium stearate or stearic acid. The tablets may be uncoated or they may be coated by known techniques to delay disintegration and absorption in the gastrointestinal tract and thereby provide a sustained action over a longer period.

Formulations for oral use may also be presented as hard gelatine capsules wherein the active ingredient is mixed with an inert solid diluent, for example calcium carbonate, calcium phosphate or kaolin, or as soft gelatine capsules wherein the active ingredient is mixed with an oil medium, for example arachis oil, liquid paraffin or olive oil.

Aqueous suspensions contain the active ingredients in admixture with excipients suitable for the manufacture of aqueous suspensions. Such excipients are suspending agents, for example sodium carboxymethyl cellulose, methylcellulose, hydroxypropylmethylcellulose, sodium alginate, polyvinylprrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol, for example polyoxyethylene sorbitol monooleate, or condensation product of ethylene oxide with partial esters derived from fatty acids and hexitol anhydrides, for example polyoxyethylene sorbitan monooleate. The said aqueous suspensions may also contain one or more preservatives, for example ethyl, or n-propyl, p-hydroxy benzoate, one or more coloring agents, one or more flavoring agents and one or more sweetening agents, such as sucrose, saccharin, or sodium or calcium cyclamate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable preparation, for example as a sterile injectable aqueous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol.

The pharmaceutical compositions may be tableted or otherwise formulated so that for every 100 parts by weight of the composition there are present between 5 and 95 parts by weight of the active ingredient and preferably between 25 and 85 parts by weight of the active ingredient. The dosage unit form will generally contain between about 1 mg and about 500 mg of the active ingredient of the formula stated above.

From the foregoing formulation discussion, it is apparent that the compositions of this invention can be administered orally or parenterally. The term parenteral as used herein includes subcutaneous injection, intravenous, intramuscular, or intrasternal injection or infusion techniques or inhalation.

To illustrate the manner in which the invention may be carried out, the following examples are given. It is understood, however, that the examples are for the purposes of illustration only.

EXAMPLE I

A number of cyclic AMP derivatives were tested in the McKenzie bioassay to determine their TSH-like activity.

McKenzie bioassay. After weaning, female mice of 14–16 grams were put on an iodine-poor diet for 14 days. They were next injected (s.c.) with 10 μg of L-thyroxine and 6–8 μc of $^{125}$I (i.p.). The three following days, they received L-thyroxine (1 mb/l.) in their drinking water. On the fourth day, the substances to be assayed were dissolved in water and injected into the tail vein. The first blood sample (0.1 ml) was taken immediately (by puncturing the orbital sinus), and consecutive samples were taken in the same way after 2 hours. The radioactivity of these samples was measured with a gamma counter (Beckman) and is expressed as percent with respect to the radioactivity of the first sample.

Results and Discussion

In the McKenzie bioassay (J.M. McKenzie, Endocrinology, 63, 372 (1958), TSH injected into mice pretreated with $^{125}$I and $T_4$ produces in 2 hours a dose-related increase of blood radioactivity due to an increased secretion of labeled iodine from the thyroid. The cyclic nucleotides as aqueous solutions (pH 7.4) were injected i.v. in a series of doses ranging from 6 mg/kg to 60 mg/kg and the results, expressed as percent increase in cpm with respect to individual blood radioactivity in cpm at zero time, are summarized in Tables 1 and 2. The data for each dose represent mean values of, on average, 6 animals.

TABLE 1

Derivatives of adenosine-3',5'-cyclic monophosphoric acid

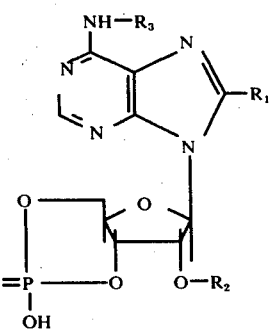

| Compound | | $R_1$ | $R_2$ | $R_3$ |
| --- | --- | --- | --- | --- |
| 1 | 8-Br—cAMP | Br | H | H |
| 2 | 8-SH—cAMP | SH | H | H |
| 3 | $N^6$,2'-O-db-8-SH—cAMP | SH | CO—$C_3H_7$ | CO—$C_3H_7$ |

TABLE 1 – Continued

Derivatives of adenosine-3',5'-cyclic monophosphoric acid

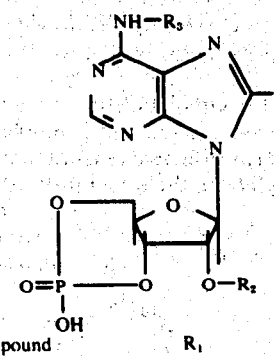

| Compound | | $R_1$ | $R_2$ | $R_3$ |
|---|---|---|---|---|
| 4 | 2'-O-mb-8-SH—cAMP | SH | CO—$C_3H_7$ | H |
| 5 | $N^6$-mb-8-SH—cAMP | SH | H | CO—$C_3H_7$ |
| 6 | 8-SMe—cAMP | SMe | H | H |
| 7 | $N^6$,2'-O-db-8-SMe—cAMP | SMe | CO—$C_3H_7$ | CO—$C_3H_7$ |
| 8 | 2'-O-mb-8-SMe—cAMP | SMe | CO—$C_3H_7$ | H |
| 9 | $N^6$-mb-8-SMe—cAMP | SMe | H | CO—$C_3H_7$ |
| 10 | 8-SBzl—cAMP | SBzl | H | H |
| 11 | $N^6$,2'-O-db-8-SBzl—cAMP | SBzl | CO—$C_3H_7$ | CO—$C_3H_7$ |
| 12 | $N^6$-mb-8-SBzl—cAMP | SBzl | H | CO—$C_3H_7$ |
| 13 | 8-OH—cAMP | OH | H | H |
| 14 | $N^6$,2'-O-db-8-OH—cAMP | OH | CO—$C_3H_7$ | CO—$C_3H_7$ |
| 15 | 8-$N_3$—cAMP | $N_3$ | H | H |
| 16 | 8-$NH_2$—cAMP | $NH_2$ | H | H |
| 17 | $N^6$,2'-O-db-8-$NH_2$—cAMP | $NH_2$ | CO—$C_3H_7$ | CO—$C_3H_7$ |

Significantly higher stimulatory effects on thyroidal function were produced by 8-SMe-cAMP, 8-$NH_2$-cAMP and 8-$N_3$-cAMP than all of the other derivatives tested. The significantly higher potency of the aforementioned compound is especially well demonstrated at the 15 mg/kg dose level. Furthermore, in contrast, other 8-substituted cAMP analogs, e.g. 8-SHcAMP and 8-OHcAMP were toxic at high doses and almost ineffective at low non-toxic doses.

The effect of these compounds on the thyroid is shown to be specific for cyclic nucleotides as opposed to non-cyclized nucleotides because 8-methylthioadenosine 5'-monophosphate (8-SMe-5'-AMP) which resembles 8-SMe-cAMP, but has an open chain, instead of a cyclic, phosphate group does not show activity.

EXAMPLE II

To evaluate the relative potency of the cyclic nucleotides in the McKenzie assay, a log dose response for TSH was determined under the same experimental conditions as used in Example I. FIG. 1 shows the curve obtained.

Figure 2:
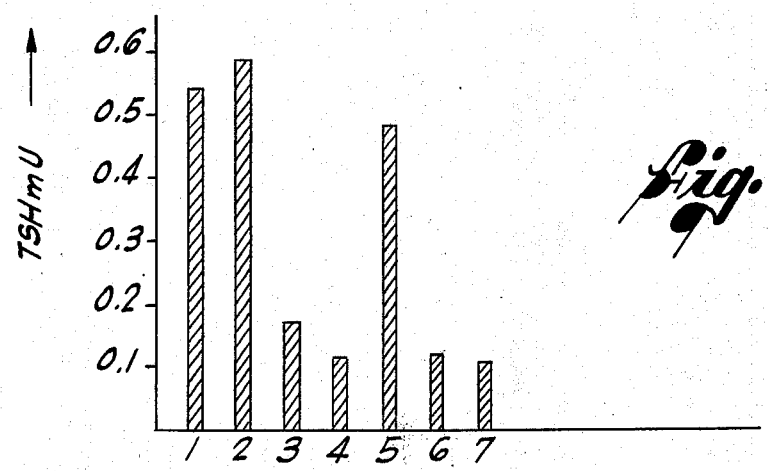
FIG. 2 shows the relative potency, expressed in mU TSH, of several cyclic AMP derivatives on thyroidal function.

Based on this TSH standard curve, it can be seen that the most potent cyclic nucleotides (8-SMe-cAMP, 8-$NH_2$-cAMP and 8-$N_3$-cAMP at 15 mg/kg) produced a stimulatory effect on the thyroid comparable to that of 0.5 mU TSH. A more comprehensive correlation between several cyclic nucleotides and TSH is shown in FIG. 2, with the legend for FIG. 2 in Table 3 below. It is apparent that the cyclic nucleotides which enhance thyroid function are the 8-SMe, the 8-$NH_2$ and the 8-$N_3$ cyclic AMP derivatives.

Table 2

McKenzie Bioassay of Cyclic Nucleotides

| | Compound | DOSE | | | |
|---|---|---|---|---|---|
| | | 60 mg/kg | 30 mg/kg | 15 mg/kg | 6 mg/kg |
| 1 | 8-Br | 488 ± 68 | 331 ± 50 | 284 ± 16 | 248 ± 30 |
| 2 | 8-SH | lethal | lethal | lethal | 136 ± 26 |
| 3 | $N^6$,2'-O-db-8-SH | 238 ± 28 | 177 ± 14 | 154 ± 7 | — |
| 4 | 2'-O-mb-8-SH | 190 ± 0 | 153 ± 12 | 155 ± 9 | — |
| 5 | $N^6$-mb-8-SH | 630 ± 36 | 342 ± 26 | 139 ± 9 | — |
| 6 | 8-SMe | — | 804 ± 52 | 645 ± 55 | 492 ± 31 |
| 7 | $N^6$,2'-O-db-8-SMe | 174 ± 23 | 125 ± 17 | 150 ± 11 | — |
| 8 | 2'-O-mb-8-SMe | 110 ± 12* | 156 ± 16 | — | — |
| 9 | $N^6$mb-8-SMe | 533 ± 74 | 204 ± 17 | 121 ± 13 | — |
| 10 | 8-SBzl | lethal | 195 ± 21 | 183 ± 13 | 135 ± 14 |
| 11 | $N^6$,2'-O-db-8-SBzl | 123 ± 7 | 141 ± 11 | 170 ± 13 | 116 ± 7 |
| 12 | $N^6$-mb-8-SBzl | 197 ± 3 | 122 ± 13 | 146 ± 10 | — |
| 13 | 8-OH | — | lethal | 114 ± 8 | — |
| 14 | $N^6$,2'-O-db-8-OH | 582 ± 66 | 500 ± 57 | 184 ± 14 | — |
| 15 | 8-$N_3$ | — | 633 ± 33 | 594 ± 61 | 227 ± 26 |
| 16 | 8-$NH_2$ | 818 ± 78* | 607 ± 42 | 663 ± 76 | 226 ± 15 |
| 17 | $N^6$,2'-O-db-8-$NH_2$ | 164 ± 6 | 146 ± 7 | — | — |
| | cAMP | 135 ± 10 | — | — | — |
| | $N^6$,2'-O-db-cAMP | 246 ± 22 | 136 ± 12 | — | — |
| | Saline (0.05 ml) | 101 ± 1 | 110 ± 1 | 107 ± 4 | |
| | 8-SMe-5'-AMP | | 112 ± 2 | | |

*45 mg/kg

Table 3

| Legend for FIG. 2 | | |
|---|---|---|
| 1 | = | 8-SMe-cAMP |
| 2 | = | 8-NH$_2$-cAMP |
| 3 | = | 8-Br-cAMP |
| 4 | = | N$^6$,2'-O-db-SH-cAMP |
| 5 | = | 8-N$_3$-cAMP |
| 6 | = | N$^6$-mb-8-SH-cAMP |
| 7 | = | N$^6$,2'-O-db-8-SMe-cAMP |

Dose — 15 mg/kg

EXAMPLE III

To confirm the foregoing results, the effect of the subject compounds on the thyroxin level in the blood was measured quantitatively by radioimmunoassay. Thyroid hormone levels (serum T$_4$) of individual 30 gram mice were measured by conventional radioimmunoassay procedures before and after i.v. injection of (a) 1 mU/mouse TSH-standard, (b) 1 mg/mouse 8-SMe-cyclic AMP, (c) 1 mg/mouse 8-SMe-5'-AMP and (d) 0.05 ml of 0.9% NaCl/mouse. Blood samples (50) were collected by orbital puncture before injection (time=t$^o$), at one hour (t$^1$) and at two hours (t$^2$) after injection. Table 4 below tabulates the results.

Table 4

| Treatment | | Radioimmunoassay of thyroid hormone | | |
|---|---|---|---|---|
| | N$^o$ | t$^o$ | t$^1$ | T$^2$ |
| a) TSH | 1 | 3.87 | 5.5 | 5.25 |
| | 2 | 4.5 | 5.75 | 6.0 |
| | 3 | 4.25 | 5.5 | 6.25 |
| | 4 | 4.75 | 6.0 | 6.25 |
| | 5 | 5.5 | 8.0 | 8.5 |
| Average ± | SE | 4.57±0.27 | 6.15$^{(xx)}$±0.47 | 6.45$^{(xx)}$±0.54 |
| | 6 | 3.7 | 6.0 | 7.0 |
| | 7 | 6.5 | 7.75 | 8.25 |
| | 8 | 4.75 | 5.5 | 6.0 |
| | 9 | 7.75 | 8.75 | 8.0 |
| b) 8-SMe-cAMP | 10 | 5.75 | 6.26 | 5.87 |
| | 11 | 5.00 | 6.75 | 5.37 |
| | 12 | 4.25 | 5.55 | 4.62 |
| | 13 | 3.37 | 5.13 | 5.62 |
| | 14 | 3.25 | 5.87 | 5.50 |
| | 15 | 4.13 | 5.75 | |
| Average ± | SE | 4.85±0.25 | 6.32$^{(xx)}$±0.41 | 6.47$^{(xx)}$±0.43 |
| | 16 | 4.62 | 4.25 | 4.62 |
| c) 8-SMe-5-AMP | 17 | 4.25 | 4.50 | 3.50 |
| | 18 | 3.75 | 3.50 | 4.75 |
| | 19 | 6.0 | 5.50 | 6.25 |
| Average ± | SE | 4.64±0.48 | 4.44$^{(ns)}$±0.41 | 4.78$^{(ns)}$±0.46 |
| | 20 | 7.0 | 7.0 | 6.5 |
| d) NaCl | 21 | 5.5 | 5.5 | 5.0 |
| | 22 | 6.25 | 6.0 | 6.0 |
| | 23 | 5.5 | 5.5 | 5.8 |
| Average ± | SE | 6.06±0.36 | 6.0$^{(ns)}$±0.36 | 5.83$^{(ns)}$±0.31 |

(X), (XX) and (NS): Student "t" test (ns) — nonsignificant, (x) = 0.05>p>0.01; (xx) = p<0.01.

Figure 3:
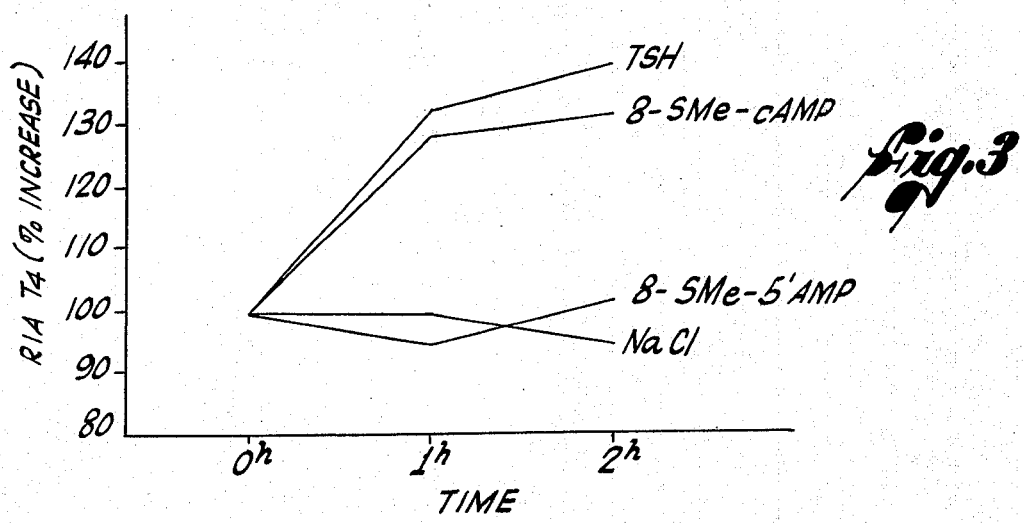
FIG. 3 shows the change in thyroid hormone ($T_4$) levels expressed in percent increase in $T_4$ after administration of TSH and 8-$SCH_3$-cyclic AMP, 8-$SCH_3$-5'AMP and NaCl.

As illustrated in table 4, 1 mg 8-SMe-cAMP produced in all animals after 1 and 2 hours, respectively, a net increase in the thyroid hormone (T$_4$) levels comparable to that produced by 1 mU of TSH. In the animals receiving NaCl, the T$_4$ level remained the same for the 2 hrs. Initial T$_4$-levels varied from animal to animal, but individual T$_4$ levels remained constant over 2 hours in the NaCl group and rose significantly in the THS and 8-SMe-cAMP treated animals. The change in T$_4$-level after 1 and 2 hours is represented graphically in FIG. 3, expressed as percent increase of T$_4$ with respect to the individual, initial (baseline) level of T$_4$.

I claim:

1. A method for stimulating the production of thyroid stimulating hormone in animals comprising administering to an animal an effective amount of a cyclic nucleotide derivative having the structural formula wherein R is selected from the group consisting of amino, thiomethyl and azido and pharmaceutically acceptable salts thereof.

* * * * *